United States Patent [19]

Truscott

[11] 4,115,696
[45] Sep. 19, 1978

[54] COMPUTED TOMOGRAPHY SCANNER

[75] Inventor: John Compton Truscott, Brookfield, Wis.

[73] Assignee: General Electric Company, Schenectady, N.Y.

[21] Appl. No.: 788,387

[22] Filed: Apr. 18, 1977

[51] Int. Cl.² .................. A61B 6/00; G01N 23/08
[52] U.S. Cl. .................. 250/445 T; 250/360
[58] Field of Search .................. 250/445 T, 360, 367, 250/366

[56] References Cited

U.S. PATENT DOCUMENTS 4,010,370  3/1977  Lemay .................. 250/445 T

Primary Examiner—Alfred E. Smith
Assistant Examiner—T. N. Grigsby
Attorney, Agent, or Firm—Ralph G. Hohenfeldt

[57] ABSTRACT

In a scanner for computed tomography an X-ray source and a multiple cell X-ray detector are mounted on a rotatable support on opposite sides of the rotational axis for orbiting about a body to thereby scan it with a diverging X-ray beam. The source and detector are each on a carriage which enables driving them jointly toward or away from the axis of rotation while the body stays fixed so that regardless of the width of the body portion its boundaries will be substantially tangent to the boundary rays of the beam and after penetrating the body the beam and the X-ray image which it entrains will always cover the entire length of the detector and use all of its cells.

4 Claims, 5 Drawing Figures

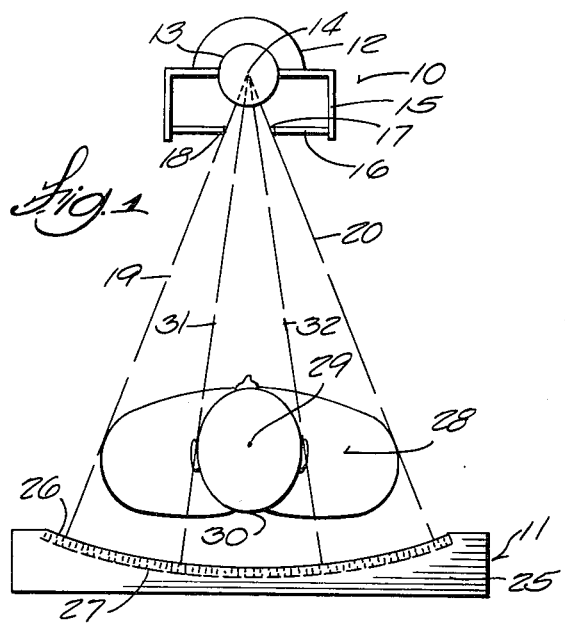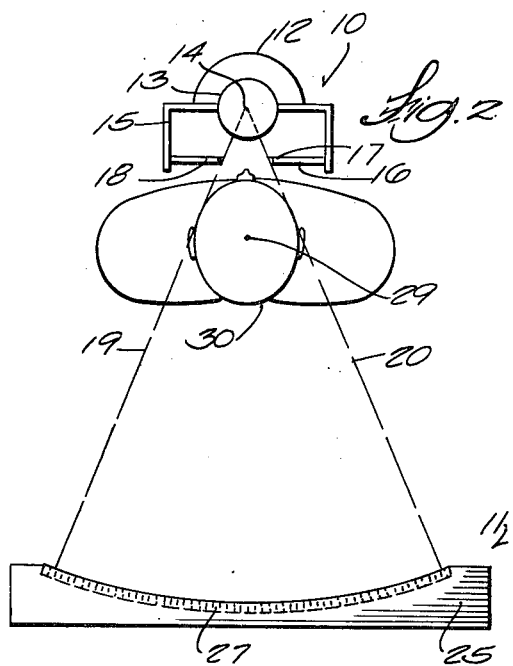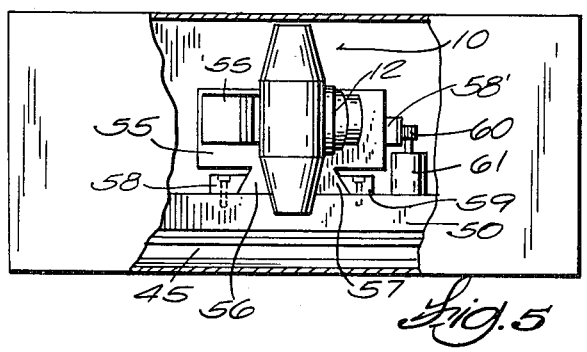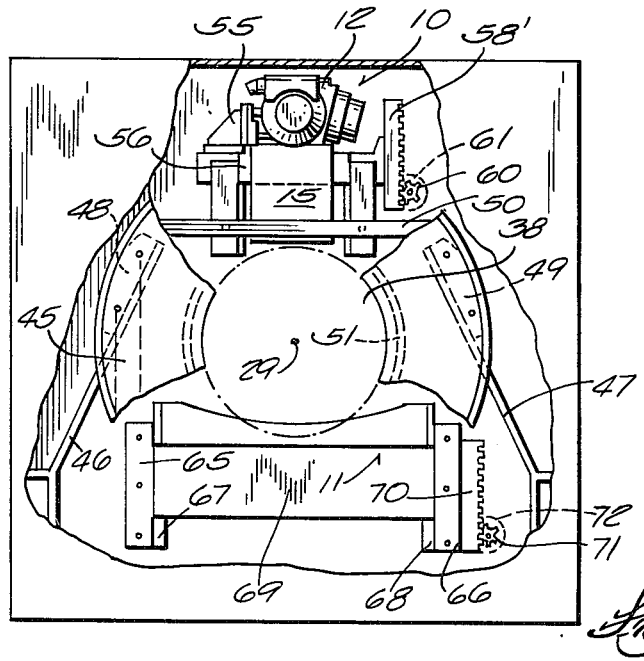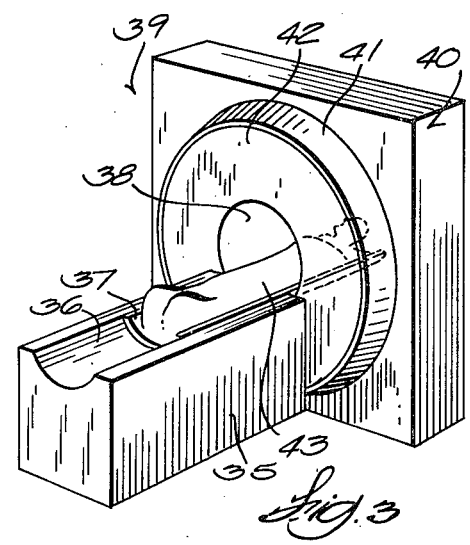

COMPUTED TOMOGRAPHY SCANNER

BACKGROUND OF THE INVENTION

This invention relates to apparatus for examining the human body with penetrating radiation such as X-ray and gamma radiation. The term X-ray will be used herein to embrace both types of radiation for the sake of brevity. The new apparatus is especially applicable to obtaining X-ray images of layers in a human body by means of computed tomography.

Background information on computed tomography may be obtained from an article entitled "Image Reconstruction From Projections" by R. Gordon, G. T. Herman and S. A. Johnson in Scientific American, Oct. 1975, Vol. 233, No. 4, p. 56. Additional background material is contained in U.S. Pat. Nos. 3,881,110 to Hounsfield et al and 3,867,634 to Hounsfield. Additionally, U.S. Pat. Nos. 4,010,370 and 4,010,371, both dated Mar. 1, 1977, show computerized tomography scanners in which the X-ray source or detector is shifted for various purposes.

The present invention is an improvement in the general type of X-ray scanning apparatus or computed tomography apparatus which is illustrated in the pending application of Kelman et al for a "Gantry for Computed Tomography", Ser. No. 771,863, filed Feb. 25, 1977. The invention may also be used in the type of X-ray scanning or computed tomography apparatus shown in the pending application of Redington et al for an "X-ray Body Scanner for Computerized Tomography", Ser. No. 723,799, filed Sept. 16, 1976. Both applications are assigned to the assignee of the present application. A typical X-ray detector array which may be used in the apparatus that will be hereinafter described may be seen in the pending application of H. R. Cummings for a "Detector Assembly for Body Scanner", Ser. No. 727,260, filed Sept. 27, 1976.

In one arrangement for performing computed tomography, a patient is supported for being translated along a longitudinal axis which is usually horizontally disposed. The axis coincides with the center of rotation of a rotatable base which has an X-ray source on one side of its center of rotation and a multiple array of X-ray detectors on the other side. A fan-shaped X-ray beam, that is thin in the longitudinal direction, is projected through the patient as the base rotates so that the detectors may develop signals indicative of X-ray transmission characteristics along a plurality of paths through a subject undergoing examination. Analog signals representative of X-ray attenuation by all of the volume elements in a layer of the body at various rotational angles are then converted to digital signals which are used by a computer to produce signals which are used for controlling a cathode ray tube to display a reconstructed image of the layer. A collimator is coupled with the X-ray source which forms the beam into a fan-shape having a layer thickness of typically about 1 cm. The boundary rays have a suitable angle of divergence for spreading over the entire length of the detector but, preferably, there should be no overlapping of the ends of the detector array. It will be evident that in such an arrangement the beam must be sufficiently divergent at the plane in which the patient is located for all parts across a patient to be within the beam and to project an image which is apportioned to the respective cells in the detector array. Algorithms to which the computer is programmed for reconstructing the image of a body layer from the digital signals produce more accurate and consistent results if all cells in the detector intercept a part of the attenuated X-ray beam. Anomalies may be produced if some of the cells receive a direct unattenuated portion of the X-ray beam or if they receive no x-radiation. It is, therefore, desirable for the scanning X-ray beam to cover the entire field of the detector at all times.

SUMMARY OF THE INVENTION

The primary object of the present invention is to provide computed tomography X-ray scanning apparatus with means for establishing the orbital X-ray source and detector in the proper geometrical relationship with the body to assure that any body layer, regardless of its width, will be projected over the entire field of the detector. A correlative of this object is to provide for obtaining X-ray attenuation data which will result in more accurate reconstruction of a computed tomography image.

In accordance with the invention, the improved scanning apparatus comprises a base that is mounted for being driven rotationally about an axis that is usually disposed substantially horizontally. A carriage is mounted on the base on one side of the rotational axis and the X-ray source is mounted on the carriage. The carriage may be driven with a servo motor to enable setting the source at the optimum distance from the body being scanned before a scan is initiated. The X-ray detector is also on a carriage which is mounted on the base. The detector carriage is also coupled with a servo motor which permits driving the detector in the radial direction relative to the body. The source and detector are adjusted coordinately so that a constant distance is maintained between the X-ray source focal spot and the detector but the distance between the focal spot and the body may be varied thereby so that a layer in the body of any width may be disposed between the boundary rays of the diverging X-ray beam at such location relative to the source that the entire detector field will be covered by the projected image.

How the foregoing and other more specific objects of the invention are achieved will be evident in the ensuing description of an embodiment of the invention in which reference will be made to the drawing.

DESCRIPTION OF THE DRAWING

FIGS. 1 and 2 are diagrams which are useful for explaining the principles of the invention;

FIG. 3 is a perspective view of a typical computed tomography X-ray scanner in which the invention may be employed;

FIG. 4 is a front elevation view of the scanning apparatus with the front of the housing partially broken away to expose the X-ray source and detector on their rotatable base; and FIG. 5 is a plan view of the apparatus shown in FIG. 4.

DESCRIPTION OF A PREFERRED EMBODIMENT

The principles of the invention will be discussed first in reference to FIGS. 1 and 2. In FIG. 1, the X-ray source is designated generally be the reference numeral 10. The detector is designated generally by the reference numeral 11. The source assembly comprises a casing which is symbolized by the semicircle marked 12. A penetrating radiation source such as X-ray tube 13 is in the casing. The focal spot of the X-ray tube is marked 14. The focal spot has a finite size but it may be treated as a point source. A collimator 15 is coupled to the X-ray tube casing and it has plates such as 16 whose edges 17 and 18 define the boundary rays 19 and 20 of the X-ray beam. Thus, the X-ray beam diverges away from focal spot 14 and may be characterized as being fan-shaped. The collimator also has plates, not shown, which are spaced apart from each other in planes that parallel the plane of the drawing such as to shape the fan-shaped beam into a thin layer. Typically, the layer may be about 1 cm thick in the direction perpendicular to the plane of the diverging beam.

Detector assembly 11 comprises a housing 25 which, in this example, may be considered to be filled with a high pressure gas that produces ion and electron pairs when penetrated with X-ray photons. The front of the detector has a thin X-ray transmissive window 26. Behind the window is an array of X-ray detecting cells 27. The cells are defined by spaced apart metal plates 20 which are electrically isolated from each other and each functions as an ionization chamber to produce analog electric signals having magnitudes corresponding with the intensity of the photons in the X-ray beam which penetrate into the respective cells. As is well known, in computed tomography the analog signals are converted to corresponding digital signals and these are supplied to a computer, not shown, which is governed by an algorithm to produce signals which may be used for driving a television monitor that displays the reconstructed image.

In further reference to FIG. 1, the X-ray source assembly 10 and detector assembly 11 are mounted for orbiting jointly around a body 28 that is being subjected to X-ray examination. Typically, the orbits of the source and detector assembly are circular and concentric. As the source and multiple cell detector orbit or scan around the body, X-ray attenuation data is gathered by the detector 11 and this analog data is converted to digital data which is processed by the computer in such way that the attenuation of small volume elements in the body may be determined. The computer produced signals, representative of attenuation by the variously located volume elements in the body, drive a raster scanned television monitor so that the X-ray image across the body layer intercepted by the thin fan-shaped beam may be visualized. In a typical computed tomography scanner, X-ray attenuation data for a layer of the body is obtained by orbiting the source and detector through 360° in one direction and then indexing the body longitudinally to the next layer whereupon the source and detector are orbited 360° in the reverse direction.

As shown in FIG. 1, the body 28 is supported at a lvel such that the axis of rotation 29 of the source and detector passes through the body. Axis 29 is perpendicular to the plane of FIG. 1.

In FIG. 1, one may see that with the X-ray source, detector and body related as they are shown, the body will be between the boundary rays 19 and 20 of the diverging X-ray beam and the full field or length of the curved multiple cell detector array will receive x-radiation which will result in attenuation data being produced. This is true for the full width of the body but if the body is advanced along axis 29 for scanning layers in the head 30 it will not be true. In this case only rays falling between rays 31 and 32 will be attenuated by the head and data for the image will only be produced in those detector cells in the arc between where rays 31 and 32 are intercepted by the cells 27. Thus, in the absence of some other means for expanding the image electronically, the layer of the head will not even fill the monitor screen so resolution of detail in the image of the layer will be reduced as compared with having the image spread over the entire screen. As mentioned earlier, there are several disadvantages to this situation. One is that the computer algorithm is not used properly in that more data points could be obtained for the head or any other narrow portion of the body than are obtained when the head is positioned relative to the source and detector as illustrated in FIG. 1. In addition, data resulting from the unattenuated beam in the angles between boundary ray 19 and ray 31 and boundary ray 20 and ray 32 is still intercepted by the opposite end regions of the curved array of detector cells. This produces a sharp transition in the data values at the interface of the beam and the sides of the head which affects the computer algorithm adversely.

In accordance with the invention, the X-ray source 10 and detector assembly 11 are constructed and arranged for being moved jointly toward and away from the body so geometrical relationships can be obtained which result in all cells in the detector array being used regardless of the width of the layer in the body being scanned. The relationship is depicted in FIG. 2.

In FIG. 2, the source 10 and, hence, focal spot 14 and detector 11 are the same distance from each other as they are in FIG. 1. The body is also maintained at the same level wherein it lies along axis 29. The divergence between boundary rays 19 and 20 is, of course, the same as in FIG. 1 since the width of the fan-shaped beam is governed by the collimator 15. Note, however, that for radiographing a narrow layer in the body such as the head 30, the margins of the layer are within boundary rays 19 and 20 in which case the full length of the multiple cell array 27 in the detector assembly 11 receives attenuated x-radiaton. The computer will respond by producing output data which will result in the image of the head layer being spread over the entire viewing screen in the monitor.

An illustrative practical embodiment of the invention will now be discussed in reference to FIGS. 3–5.

FIG. 3 shows a typical scanner and patient handling apparatus for performing computed tomography. It comprises a floor mounted base 35 in which there is a saddle 36. A curved table 37 is mounted for being translated under power or indexed longitudinally. Table 37 is preferably made of a rigid plastic which does not attenuate x-radiation significantly. The translatable table top 37 enables supporting the patient in cantilever fashion as shown. Thus, the patient extends through a hole 38 in a so-called gantry 39. More details on a suitable gantry may be seen in the above cited copending application of Kelman et al. The gantry comprises an enclosure or housing 40. It has a forwardly extending rim 41 which is fixed to the housing. A decorative plastic annular shield 42 defines the opening 38 through which the patient extends. The longitudinal axis corresponding with axis 29 in FIGS. 1 and 2 is directed lengthwise of the patient 43 undergoing examination. The scanning mechanism which is in housing 40 and is pertinent to the present invention may be seen better in FIGS. 4 and 5.

Referring to FIG. 4, the scanning apparatus comprises a flat circular plate 45 which stands upright and is supported by a pair of legs 46 and 47 which have flanges 48 and 49, respectively, for bolting them to the plate.

On the remote side of plate 45 one of the members 50 of a rotatable base or frame is visible. There is a large annular ball bearing 51 mounted in plate 45 and shown in dashed lines in FIG. 4. The bearing surrounds the large circular opening 38 through which the patient extends. The rotating frame comprised of members such as 50 is rotatable on bearing 51. The motor for driving the frame rotationally is not shown.

X-ray source 10 and the detector 11 are mounted on the rotating frame or base for moving in selectively opposite directions jointly and with a constant distance between them to achieve the purposes discussed relative to FIGS. 1 and 2. Considering the X-ray source first, the X-ray tube casing 12 and the tube within it are mounted on a base 55 as can be seen in FIGS. 4 and 5. The base 55 has dovetails 56 and 57 fastened to it which are adapted to move vertically with the base in cooperation with guide means in the form of dovetail blocks 58 and 58' which are fastened to the base which rotates about axis 29. The collimator assembly 15 projects vertically between the dovetail guides such as to enable the fan-shaped X-ray beam to be projected toward the detector assembly 11. A gear rack 59 is shown schematically as being fastened to supporting base 55 for the X-ray tube casing. The gear rack is engaged by a pinion 60 that is driven by a servo motor 61. The driving arrangement is intended to by symbolic of one that will advance in definite increments which is accomplished by using a stepping type of servo motor 61 preferably. Of course, as explained earlier, the position of the X-ray source is only adjusted before a scan is initiated and when setting up to scan a body layer whose width is to be fit substantially tangential to and between the boundary rays 19 and 20 of the X-ray beam.

The detector assembly is also shown schematically in FIG. 4 as being mounted on the rotating base. The support for translating the detector comprises a pair of dovetails 65 and 66 which are fastened to the rotating base. They cooperate with members 67 and 68 which are slideable in the dovetails and support a plate 69 on which the detector assembly and data acquisition system, not shown are supported. The driving mechanism is symbolized by a gear rack 70 which is effectively fastened to plate 69 and constitutes part of the carriage for the detector assembly. Gear rack 70 is engaged by a pinion 71 on the shaft of a servo motor 72. The servo motor is controllable to move the detector carriage in steps corresponding with the number of steps and direction in which the X-ray source is moved so the source and detector are always at the same distance from each other regardless of how they relate to the position of a patient who is disposed in circular opening 38.

The control system for the servo motor is not shown but such system can be readily designed by anyone reasonably skilled in the electronic arts. An essential attribute of the system is that is should control the X-ray source and X-ray detector to move in synchronism while maintaining the distance between them constant so the X-ray beam diverges over the whole span of detector cells.

Those skilled in the art will appreciate that the X-ray source 10 with its collimator and the diametrically opposite detector assembly 11 could be mechanically interconnected so that one servo motor could drive one of the source and detector and the other of the source and detector would necessarily move an equal distance to thereby maintain a constant distance between them.

Although a particular embodiment of the invention has been described in some detail, such description is intended to be illustrative rather than limiting, for the invention may be variously embodied and it to be limited only by interpretation of the claims which follow.

1. Apparatus for examining a layer in a body with X-radiation comprising:
    means rotatable about an axis on which an examination body may be disposed,
    a source for projecting a fan-shaped beam of X-radiation originating substantially from a point, said beam being coincident with said layer and having boundary rays that diverge at a fixed angle from said point in the plane of said layer,
    a generally circumferentially distributed array of X-ray detector means on a side of said axis opposite from said source disposed across said diverging beam for detecting radiation between said boundary rays after said radiation has passed across said axis, and
    means for mounting said source and detector means on said rotatable means for orbiting jointly about said axis and means operable to shift said source and detector means jointly in the plane of said layer to thereby enable disposing a layer regardless of its width substantially tangentially to said boundary rays so that the projection of said layer will cover substantially the whole array of detector means.

2. The apparatus as in claim 1 wherein said means which are operable to shift said source and detector means jointly comprise reversing motor means and means operatively coupling said motor means to said detector means and source for effecting their simultaneous shifting in the same direction in said plane in response to operation of said motor means in either direction.

3. The apparatus as in claim 1 wherein said means which are operable to shift said source and detector means jointly comprise reversible first and second synchronously operable motor means, means for operatively coupling said first motor means to said X-ray source and means for operatively coupling said second motor means to said detector means.

4. The apparatus as in claim 1 wherein said array of detector means are unspaced from each other and are disposed along an arc having radii converging generally in the direction of said X-ray source point.

* * * * *